US009504799B2

(12) United States Patent
Hardin et al.

(10) Patent No.: US 9,504,799 B2
(45) Date of Patent: Nov. 29, 2016

(54) HUMIDIFIER BYPASS VALVE

(75) Inventors: William Russell Hardin, Carlsbad, CA (US); Ian Michael Cadieux, San Diego, CA (US); Francisco Javier Lopez, Carlsbad, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 361 days.

(21) Appl. No.: 13/879,850

(22) PCT Filed: Oct. 17, 2011

(86) PCT No.: PCT/IB2011/054585
§ 371 (c)(1),
(2), (4) Date: Apr. 17, 2013

(87) PCT Pub. No.: WO2012/052903
PCT Pub. Date: Apr. 26, 2012

(65) Prior Publication Data
US 2013/0199524 A1 Aug. 8, 2013

Related U.S. Application Data

(60) Provisional application No. 61/405,341, filed on Oct. 21, 2010.

(51) Int. Cl.
*A61M 16/16* (2006.01)
*A61M 16/08* (2006.01)
(Continued)

(52) U.S. Cl.
CPC ..... *A61M 16/0816* (2013.01); *A61M 16/0057* (2013.01); *A61M 16/0875* (2013.01);
(Continued)

(58) Field of Classification Search
CPC .... A61M 15/00; A61M 16/00; A61M 16/08; A61M 16/0808; A61M 16/10; A61M 16/1075; A61M 16/109; A61M 16/16; A61M 16/162; A61M 16/164; A61M 16/167; A61M 16/204; A61M 16/205; A61M 16/208; A61M 16/209; A61M 39/26; A61M 16/0057; A61M 16/0816; A61M 16/0875; A61M 16/20; A61M 16/0003; A61M 16/0051; A61M 16/0066; A61M 16/161; A62B 7/00; A62B 9/02; A62B 9/04; B01D 47/02; B63C 11/02; B63C 11/28; F24F 6/12
USPC ........... 128/200.13, 200.24, 200.27, 203.16, 128/203.17, 203.27, 204.13, 204.14, 128/204.17, 204.18, 205.24, 205.27; 261/104, 107, 119.1, 120, 122.1, 128, 261/129, 142, 154, 62, 64.1, 65, 66, 72.1, 261/99, DIG. 65
See application file for complete search history.

(56) References Cited

U.S. PATENT DOCUMENTS 4,010,748 A * 3/1977 Dobritz ................. A61M 16/16
128/203.27
6,550,476 B1 4/2003 Ryder
(Continued)

FOREIGN PATENT DOCUMENTS

DE 102005042181 A1 4/2006
DE 102008057345 B3 4/2010
(Continued)

*Primary Examiner* — Annette Dixon

(57) ABSTRACT

A valve (30) for controlling a flow of fluid, the valve having a conduit, first valve portion having an inlet, a first humidifier interface, and a first conduit opening to the conduit. The first valve portion defines a switchable flow path between the inlet and either the first humidifier interface or the first conduit opening. A second valve portion has an outlet, a second humidifier interface, and a second conduit opening to the conduit. The second valve portion defines a switchable flow path between the outlet and either the second humidifier interface or the second conduit opening. Responsive to the first and/or second humidifier interfaces being connected to a humidifier chamber, the fluid flows from the inlet to the outlet through the humidifier chamber, and responsive to the first and second humidifier interfaces being disconnected from the humidifier chamber, the fluid flows from the inlet to the outlet through the conduit.

15 Claims, 5 Drawing Sheets

(51) Int. Cl.
 *A61M 16/20* (2006.01)
 *A61M 16/14* (2006.01)
 *A61M 16/10* (2006.01)
 *A61M 16/00* (2006.01)

(52) U.S. Cl.
 CPC ....... *A61M16/109* (2014.02); *A61M 16/1075* (2013.01); *A61M 16/16* (2013.01); *A61M 16/20* (2013.01); *A61M 16/208* (2013.01); *A61M 16/0066* (2013.01); *A61M 16/0808* (2013.01); *A61M 16/105* (2013.01); *A61M 2202/025* (2013.01); *A61M 2202/0208* (2013.01); *A61M 2205/3368* (2013.01)

(56) References Cited

U.S. PATENT DOCUMENTS

| | | |
|---|---|---|
| 7,686,014 B2 | 3/2010 | Boehm |
| 8,833,367 B2 | 9/2014 | Kwok |
| 2001/0050080 A1* | 12/2001 | Seakins ............... A61M 16/08 128/203.16 |
| 2005/0188990 A1* | 9/2005 | Fukunaga ............ A61M 16/08 128/204.18 |
| 2006/0029837 A1 | 2/2006 | Sennoun et al. |
| 2007/0144516 A1 | 6/2007 | Doyle |
| 2007/0157928 A1 | 7/2007 | Pujol |
| 2008/0302362 A1* | 12/2008 | Kwok ................. A61M 16/16 128/203.16 |
| 2010/0122702 A1 | 5/2010 | Reinboth |

FOREIGN PATENT DOCUMENTS

| | | |
|---|---|---|
| EP | 0992259 A1 | 4/2000 |
| EP | 1138341 A2 | 10/2001 |
| EP | 1262208 A2 | 12/2002 |
| JP | 2002233573 A | 8/2002 |
| JP | 2008508958 A | 3/2008 |
| WO | 2004098689 A1 | 11/2004 |
| WO | 2007038690 A2 | 4/2007 |

* cited by examiner

HUMIDIFIER BYPASS VALVE

BACKGROUND OF THE INVENTION

1. Field of the Invention

The invention relates to a bypass valve associated with a humidifier and a respiration circuit for directing a flow of fluid from a ventilator to a subject.

2. Description of the Related Art

A subject connected to a prior art ventilator 2 (see FIG. 1) is typically connected thereto via a prior art respiration circuit 4 (see FIG. 1) having a set of tubes. As shown in FIG. 1, the prior art respiration circuit 4 may be operatively connected to a prior art humidifier 6 having a prior art humidifier chamber 8 that humidifies the otherwise relatively-dry air generated by the prior art ventilator 2. A prior art first tube 10 of the set of tubes connects the ventilator to the prior art humidifier chamber 8 and a prior art second tube 12 connects the prior art humidifier chamber 8 to a patient mask or endo-tracheal (ET) tube. When subjects are to be transported, the prior art humidifier 6 is typically disconnected from the prior art respiration circuit 4 and left behind because of the lack of available AC power source to power the prior art humidifier 6 during transport as well as the excessive size and weight of the humidifier. Furthermore, if the prior art humidifier chamber 8 is not disconnected during transport, water from the prior art humidifier chamber 8 may leak into and occlude the subject's breathing path in the respiration circuit. Avoiding or correcting this hazard requires disconnecting the circuit 4 from the prior art humidifier chamber 8, thereby introducing bio hazards and disrupting therapy.

The disconnection process includes disconnecting the prior art first tube 10 from the prior art ventilator 2, disconnecting the prior art second tube 12 from the prior art humidifier chamber 8, and connecting the prior art second tube 12 to the prior art ventilator 2, as shown in FIG. 2. However, the process of disconnecting the humidifier from the respiration circuit may disrupt the subject's therapy, may cause alarm signals to be generated in the ventilator because of the disruption, and may also cause bacterial/viral contaminants to be introduced into the subject's airway.

SUMMARY OF THE INVENTION

One aspect of the invention relates to a valve configured to control a flow of fluid (i.e. gas) through the valve. The valve has a conduit and a first valve portion disposed at a first end of the conduit. The first valve portion has an inlet configured to interface with a respiration circuit, a first humidifier interface configured to be removably connected to a humidifier chamber, and a first conduit opening in fluid communication with an interior of the conduit. The first valve portion is configured to define a switchable flow path between the inlet and either the first humidifier interface or the first conduit opening. The valve also has a second valve portion disposed at a second end of the conduit. The second valve portion has an outlet configured to interface with a respiration circuit, a second humidifier interface configured to be removably connected to the humidifier chamber, and a second conduit opening in fluid communication with the interior of the conduit. The second valve portion is configured to define a switchable flow path between the outlet and either the second humidifier interface or the second conduit opening. The first valve portion and the second valve portion are configured such that 1) responsive to the first humidifier interface and the second humidifier interface being connected to the humidifier chamber, a flow path is formed from the inlet to the outlet through the humidifier chamber, and 2) responsive to the first humidifier interface and/or the second humidifier interface being disconnected from the humidifier chamber, a flow path is formed from the inlet to the outlet through the conduit.

Another aspect of the invention relates to a method for controlling a flow of fluid through a valve. The method includes the step of receiving a flow of fluid from a respiration circuit at a first valve portion disposed at a first end of a conduit. The first valve portion has an inlet configured to interface with the respiration circuit, a first humidifier interface configured to be removably connected to a humidifier chamber, and a first conduit opening in fluid communication with the interior of the conduit. The first valve portion is configured to define a switchable flow path between the inlet and either the first humidifier interface or the first conduit opening. The method also includes the step of directing the flow of fluid between the inlet and the first humidifier interface to the humidifier chamber. The method also includes the step of receiving the flow of fluid from the humidifier chamber at a second valve portion disposed at a second end of the conduit. The second valve portion has a second humidifier interface configured to be removably connected to the humidifier chamber, a second conduit opening in fluid communication with the interior of the conduit, and an outlet configured to interface with a respiration circuit. The second valve portion is configured to define a switchable flow path between the outlet and either the second humidifier interface or the second conduit opening. The method further includes the steps of covering the first humidifier interface and the second humidifier interface and directing the flow of fluid from the inlet of the first valve portion to the outlet of the second valve portion through the conduit.

Yet another aspect of the invention relates to a valve configured to control a flow of fluid through the valve. The valve includes a first valve portion having means for receiving the flow of fluid from a respiration circuit and first means for interfacing with a humidifier chamber to communicate the flow of fluid to the humidifier chamber. The valve also includes a second valve portion having second means for interfacing with the humidifier chamber to receive the flow of fluid from the humidifier chamber and means for directing the flow of fluid to the respiration circuit. The valve also includes means for connecting the first valve portion and the second valve portion. The first valve portion is disposed at a first end of the means for connecting for fluid communication therewith and the second valve portion is disposed at a second end of the means for connecting for fluid communication therewith, wherein the first valve portion defines a switchable flow path between the means for receiving and either the first means for interfacing or the means for connecting, and wherein the second valve portion defines a switchable flow path between the means for directing and either the second means for interfacing or the means for connecting. The valve further includes means for switching a flow path between 1) a first flow path formed from the means for receiving to the means for directing through the humidifier chamber and 2) a second flow path formed from the means for receiving to the means for directing through the means for connecting.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment of the invention, the structural components illustrated herein are drawn to scale. It is to be expressly understood, however, that the drawings are for the purpose of illustration and description only and are not a limitation of the invention. In addition, it should be appreciated that structural features shown or described in any one embodiment herein can be used in other embodiments as well. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

Figure 1:
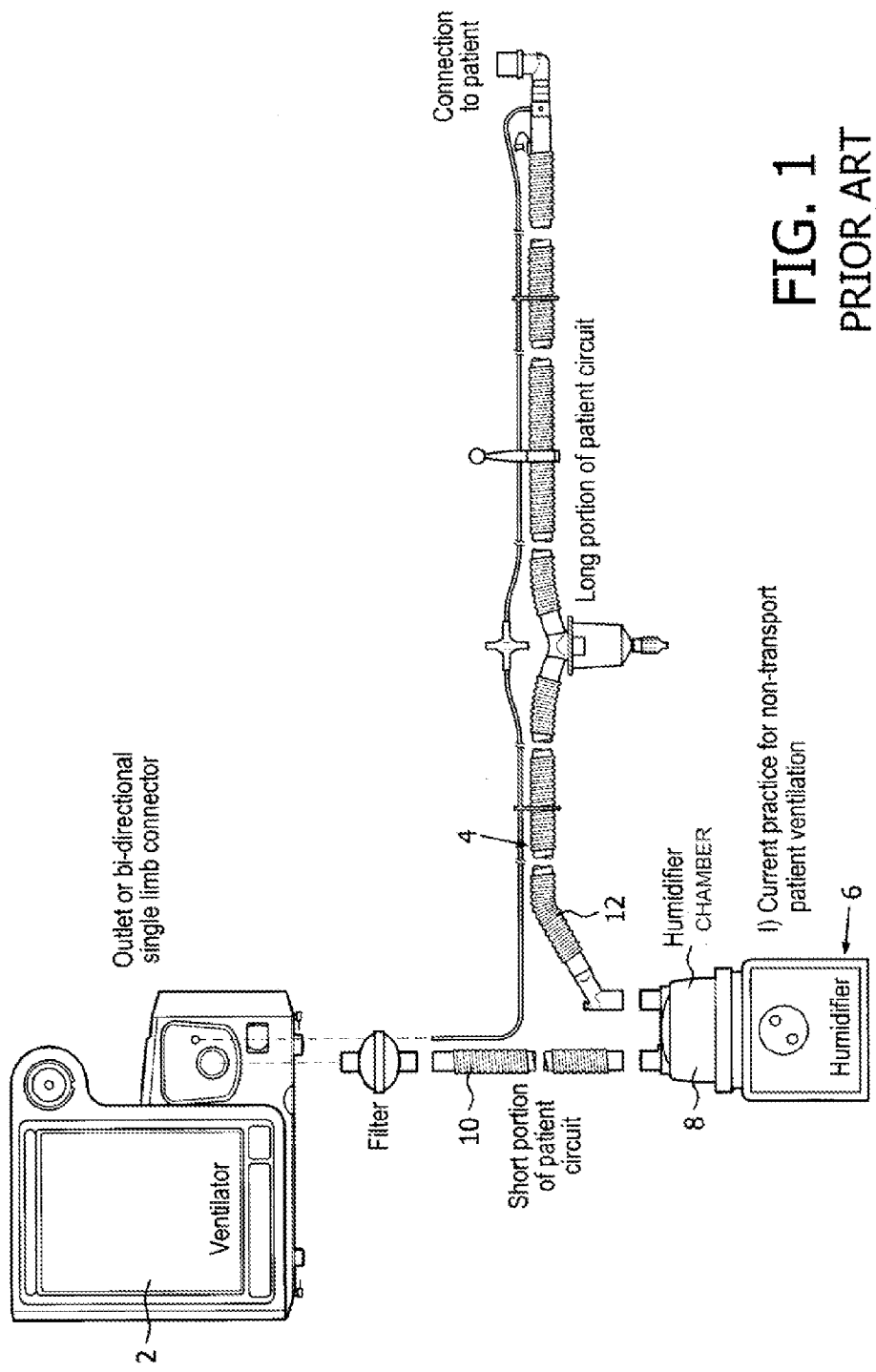
FIG. 1 illustrates a conventional connection among a ventilator, a humidifier chamber, and a respiration circuit.
Figure 2:
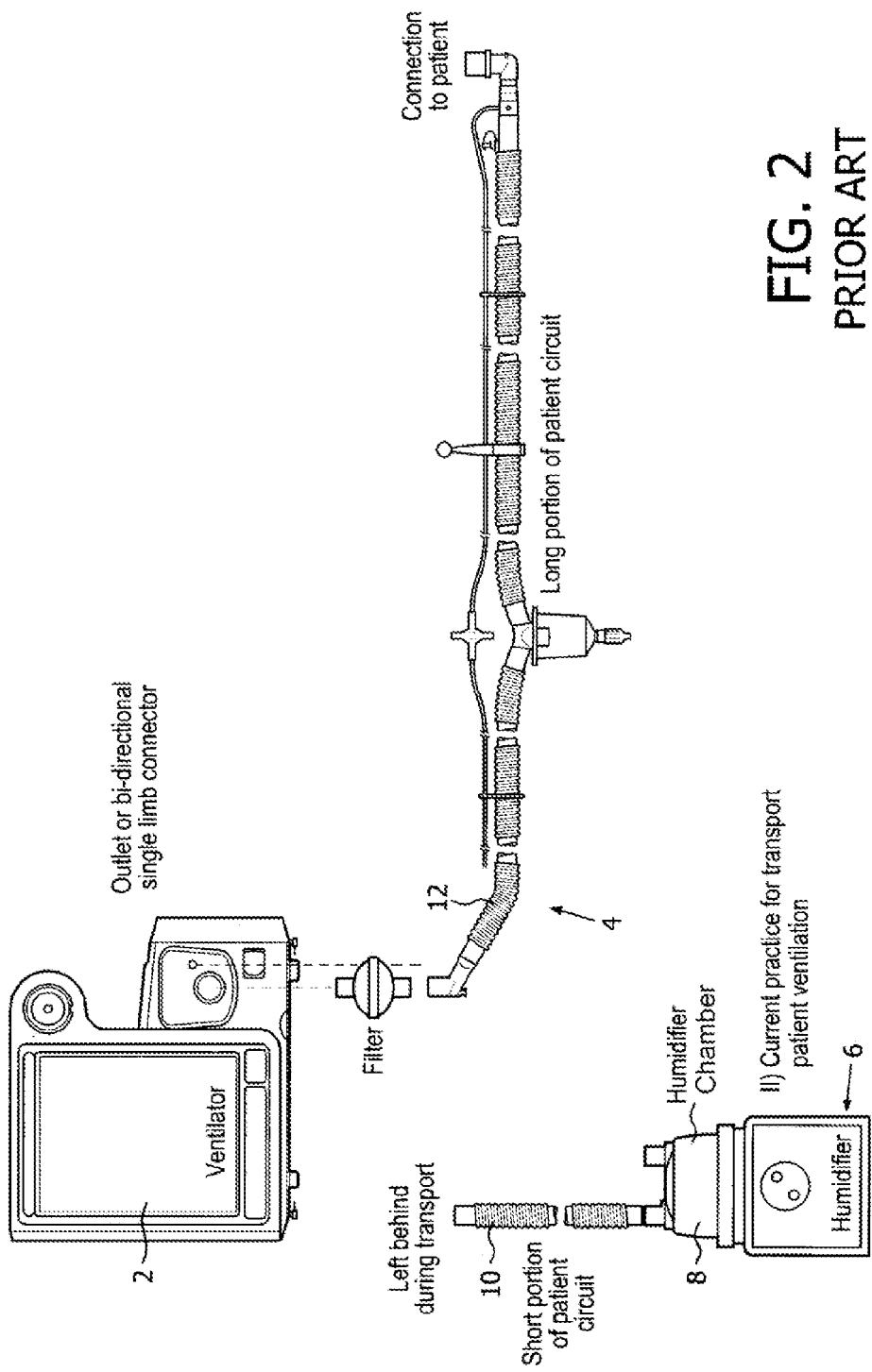
FIG. 2 illustrates a conventional connection between the ventilator and the respiration circuit with the humidifier chamber disconnected from the respiration circuit.
Figure 3:
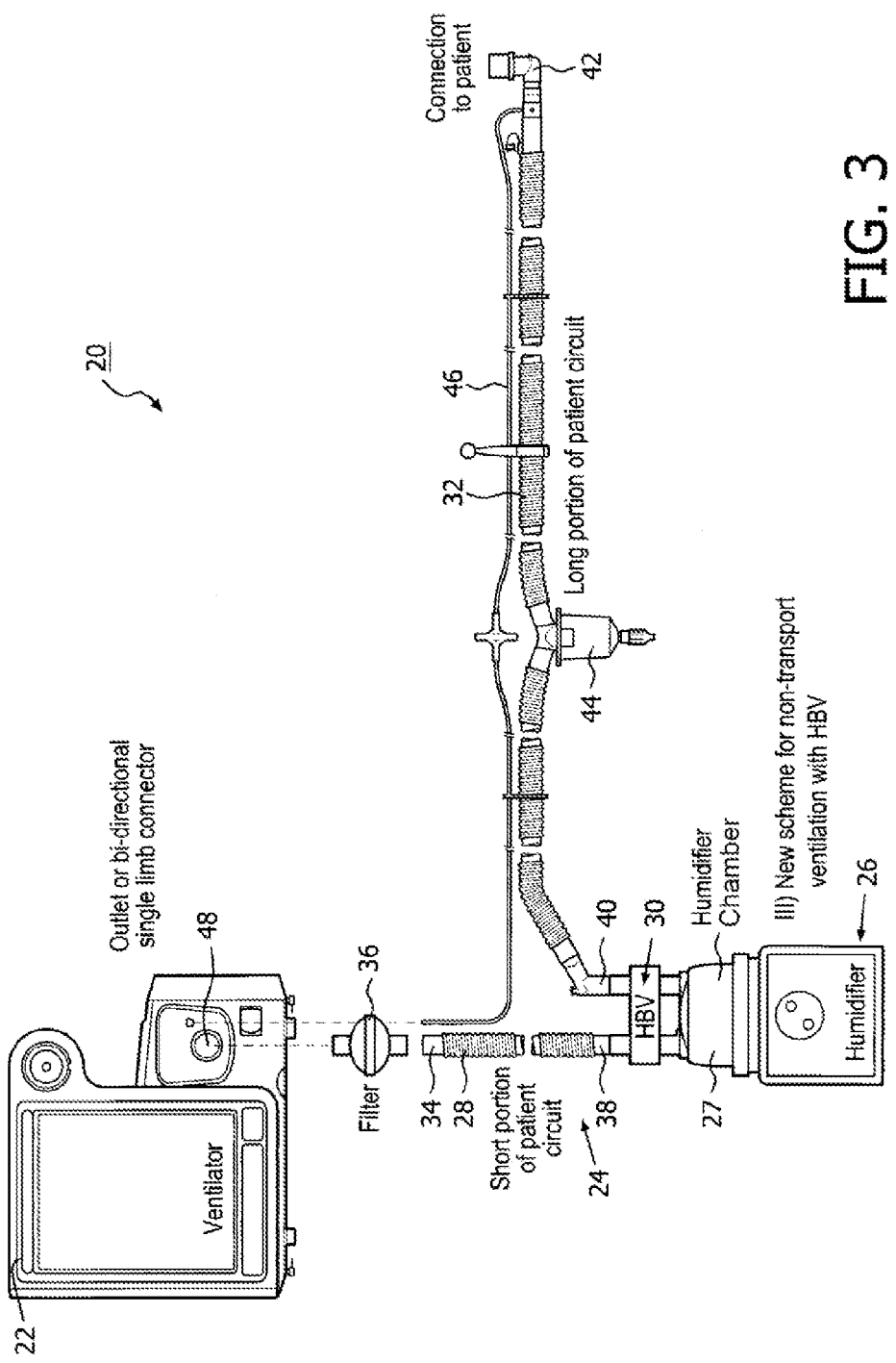
FIG. 3 illustrates a connection among the ventilator, humidifier chamber, and respiration circuit using a bypass valve in accordance with an embodiment.

FIG. 3 illustrates a system 20 for ventilating a subject in accordance with an embodiment. The system 20 includes a ventilator 22 configured to pressurize fluid (e.g., gas) from a body of fluid (not shown) to provide a flow of fluid to an airway of the subject to mechanically facilitate the respiration of the subject. The ventilator 22 may deliver fluid to the subject via a respiration circuit 24. The respiration circuit 24 may include a first tube 28 configured to communicate the flow of fluid from the ventilator 22 to a humidifier 26 having a humidifier chamber 27 to humidify the otherwise relatively-dry fluid from the ventilator 22. The first tube 28 may be about 1-2 ft. in length in some embodiments, although it is contemplated that the length can vary in other embodiments. The respiration circuit 24 may also include a second tube 32 configured to communicate the flow of fluid from the humidifier chamber 27 to the subject. The second tube 32 may be longer than the first tube 28 and may be about 6-12 ft. in length in some embodiments, although it is contemplated that the length can vary in other embodiments. The first and second tubes 28, 32 may be a flexible tubing and may be any type of tubing that enables fluid to be communicated. The first and second tubes 28, 32 may be disposable, cleanable, or sterilizable (e.g., via cold sterilization or heat sterilization). In one embodiment, the first and second tubes 28, 32 may have a diameter of about 22 mm. However, it is contemplated that the diameter of the first and second tubes 28, 32 may vary in other embodiments. The first and second tubes 28, 32 may be made of silicone rubber, high density polyethylene, thermoplastic elastomer, other materials, or a combination thereof.

In the illustrated embodiment, a bypass valve 30 is connected to the respiration circuit 24 and is removably connected to the humidifier chamber 27 to facilitate the connection between the respiration circuit 24 and the humidifier chamber 27 and to control the flow of fluid therethrough. The first tube 28 has a first end 34 that is connected to the ventilator 22 via an optional filter 36. The filter 36 is configured to remove contaminants from the gas communicated from the ventilator 22 to the respiration circuit 24. The first tube 28 has a second end 38 that is fluidly connected to the bypass valve 30, the bypass valve 30 being configured to fluidly connect the first tube 28 to the humidifier chamber 27. The second tube 32 has a first end 40 that is fluidly connected to the bypass valve 30, the bypass valve 30 being configured to fluidly connect the second tube 32 to the humidifier chamber 27. The bypass valve 30 will be described in more detail later. A second end 42 of the second tube 32 fluidly connects the respiration circuit 24 to a patient interface (not shown) for directing compressed the fluid toward and/or into the subject's airway. The patient interface may be any appliance, either invasive or non-invasive, such as a nasal mask, nasal/oral mask, total face mask, nasal cannula, endotracheal tube, or tracheal tube, suitable for communicating fluid to the airway of the subject. As used herein, the term "connection" may also include fluid connection or communication between components.

In the embodiment shown in FIG. 3, the humidifier 26 includes the humidifier chamber 27 configured to hold a reservoir of water. In one embodiment, the top of the humidifier chamber 27 is formed from a polymeric material, such as a clear polycarbonate material with a metal bottom plate to facilitate heating. However, it is contemplated that other materials may be used in other embodiments. The humidifier chamber 27 may be removable from the humidifier 26 for refilling the reservoir of liquid. The humidifier 26 may be of any type of humidifier capable of humidifying the fluid delivered to the subject. For example, the humidifier 26 may be of the type sold as Fisher Paykel 850 or others.

The body of fluid that supplies the ventilator 22 with fluid may include sources of breathable gas. The gas may include typical ambient gas, gas having a specific composition (e.g., purified oxygen, medical air, a mixture of helium and oxygen, and/or other specific compositions), and/or other sources of pressured gas. To pressurize the gas, gas sources may be stored under pressure, pressurized mechanically within gas sources, and/or otherwise pressurized. In one embodiment, at least a portion of the body of fluid is already pressurized before it is introduced to the ventilator 22. In some embodiments, a gas flow generator may provided in the ventilator 22 to create a flow of fluid at a pressure greater than ambient atmosphere. The gas flow generator may be, just for example, a compressor, a fan, an impeller, a blower, piston, or bellows.

Depending on the type of system 20 used, a water trap 44 may be provided in the respiration circuit 24. In one embodiment, a proximal pressure line 46 is provided in the system 20. The ventilator 22 may also include alarms that may be activated to generate signals when the respiration circuit 24 is disconnected at any point such that the delivery of fluid to the subject is disrupted.

It is contemplated that the ventilator 22 may be any type of ventilator operable to provide fluid to the subject. For example, the ventilator 22 may be of the type sold as Philips V200, Philips V60, Philips Trilogy, PB/Covidien 840, Viasys Avea, Carefusion ENVE, Maquet Servo-I, Draeger Evita, Draeger XL-500, Draeger Infinity, Hamilton G5, or other types. The ventilator 22 may also be of the type described in U.S. Application Publication No. 2007/0144516 or U.S. Application Publication No. 2007/0157928.

In the embodiment shown in FIG. 3, the ventilator 22 is provided with a ventilator outlet port 48 configured to be coupled to the filter 36. In embodiments where the filter 36 is eliminated, the ventilator outlet port 48 may be directly coupled to the first tube 28.

Figure 4:
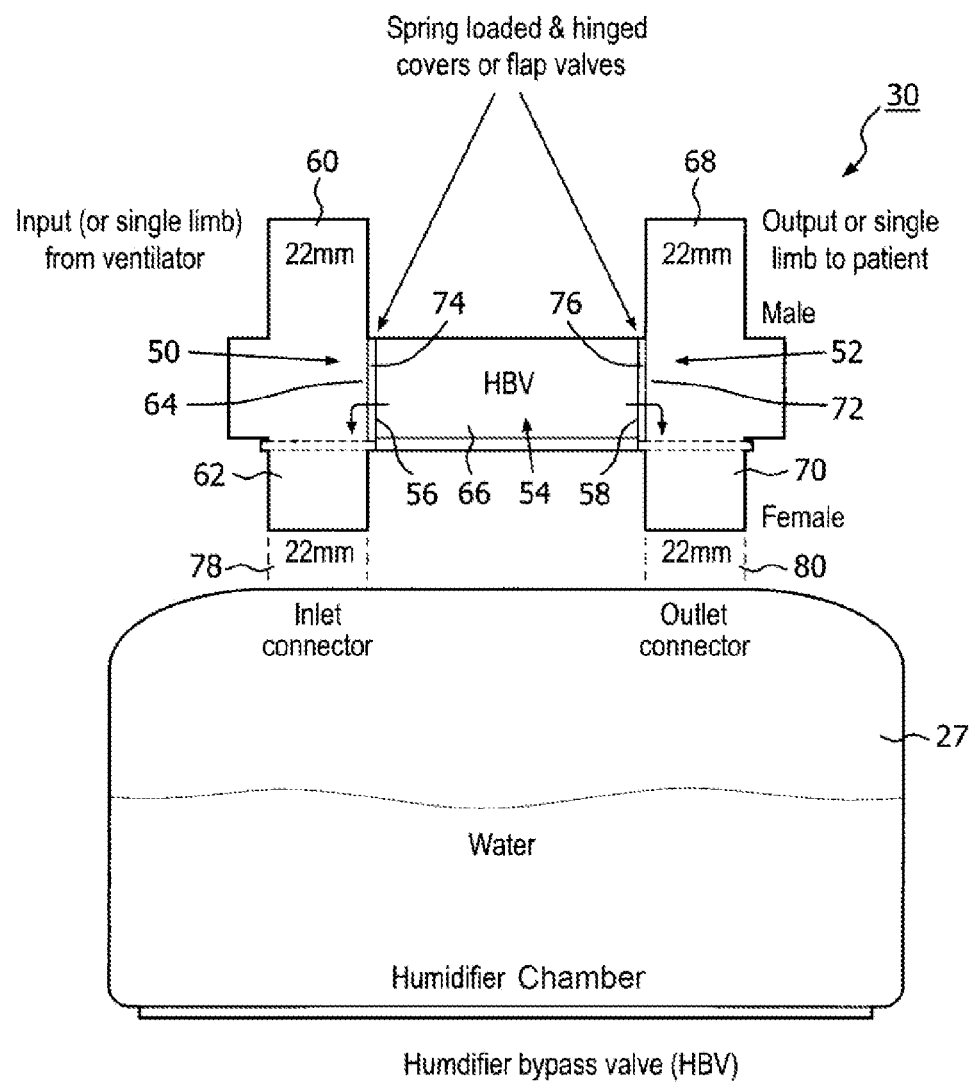
FIG. 4 illustrates the bypass valve in accordance with an embodiment.

FIG. 4 shows an embodiment of the bypass valve 30. The bypass valve 30 includes a first valve portion 50, a second valve portion 52, and a conduit 54 provided between the first valve portion 50 and the second valve portion 52. In the illustrated embodiment, the conduit 54 connects the first valve portion 50 and the second valve portion 52. The first valve portion 50 is disposed at a first end 56 of the conduit 54. The second valve portion 52 is disposed at a second end 58 of the conduit 54. The first valve portion 50 has an inlet 60 configured to interface with the respiration circuit 24 and a first humidifier interface 62 configured to be removably connected to the humidifier chamber 27. The first valve portion 50 also has a first conduit opening 64 in fluid communication with an interior 66 of the conduit 54. The first valve portion 50 is configured to define a switchable flow path between the inlet 60 and either the first humidifier interface 62 or the first conduit opening 64. The second valve portion 52 has an outlet 68 configured to interface with the respiration circuit 24 and a second humidifier interface 70 configured to be removably connected to the humidifier chamber 27. The second valve portion 52 also has a second conduit opening 72 in fluid communication with the interior 66 of the conduit 54. The second valve portion 52 is configured to define a switchable flow path between the outlet 68 and either the second humidifier interface 70 or the second conduit opening 72. The first valve portion 50 and the second valve portion 52 are configured such that responsive to the first humidifier interface 62 and the second humidifier interface 70 being connected to the humidifier chamber 27, a flow path is formed from the inlet 60 to the outlet 68 through the humidifier chamber 27. The first valve portion 50 and the second valve portion 52 are further configured such that responsive to the first humidifier interface 62 and/or the second humidifier interface 70 being disconnected from the humidifier chamber 27, a flow path is formed from the inlet 60 to the outlet 68 through the conduit 54. The bypass valve 30 may be self-sealing to provide air tight and/or liquid tight closure during operation thereof.

In the illustrated embodiment, the flow path is switchable by a first valve member 74 and a second valve member 76. The first valve cover or member 74 is provided in the first valve portion 50 and is configured to be moveable between 1) a first position wherein the first valve member 74 covers the first humidifier interface 62 and 2) a second position wherein the first valve member 74 covers the first conduit opening 64. Accordingly, when the first valve member 74 is in the first position, the flow path is between the inlet 60 and the first conduit opening 64. In contrast, when the first valve member 74 is in the second position, the flow path is between the inlet 60 and the first humidifier interface 62.

The second valve member 76 is provided in the second valve portion 52 and is configured to be moveable between 1) a first position wherein the second valve member 76 covers the second humidifier interface 70 and 2) a second position wherein the second valve member 76 covers the second conduit opening 72. Accordingly, when the second valve member 76 is in the first position, the flow path is between the outlet 68 and the second conduit opening 72. In contrast, when the second valve member 76 is in the second position, the flow path is between the outlet 68 and the second humidifier interface 70.

The first valve member 74 and the second valve member 76 may move between the second and first positions together and/or independently. Accordingly, when the first valve member 74 and the second valve member 76 are both in the first position, the fluid flows from the inlet 60 to the outlet 68 through the conduit 54 of the bypass valve 30. And when the first valve member 74 and the second valve member 76 are both in the second position, the fluid flows from the inlet 60 to the outlet 68 through the humidifier chamber 27. As used herein with respect to the first valve member 74 and the second valve member 76, the term "cover" may refer to providing either an air tight closure or liquid tight closure, or both.

Figure 5:
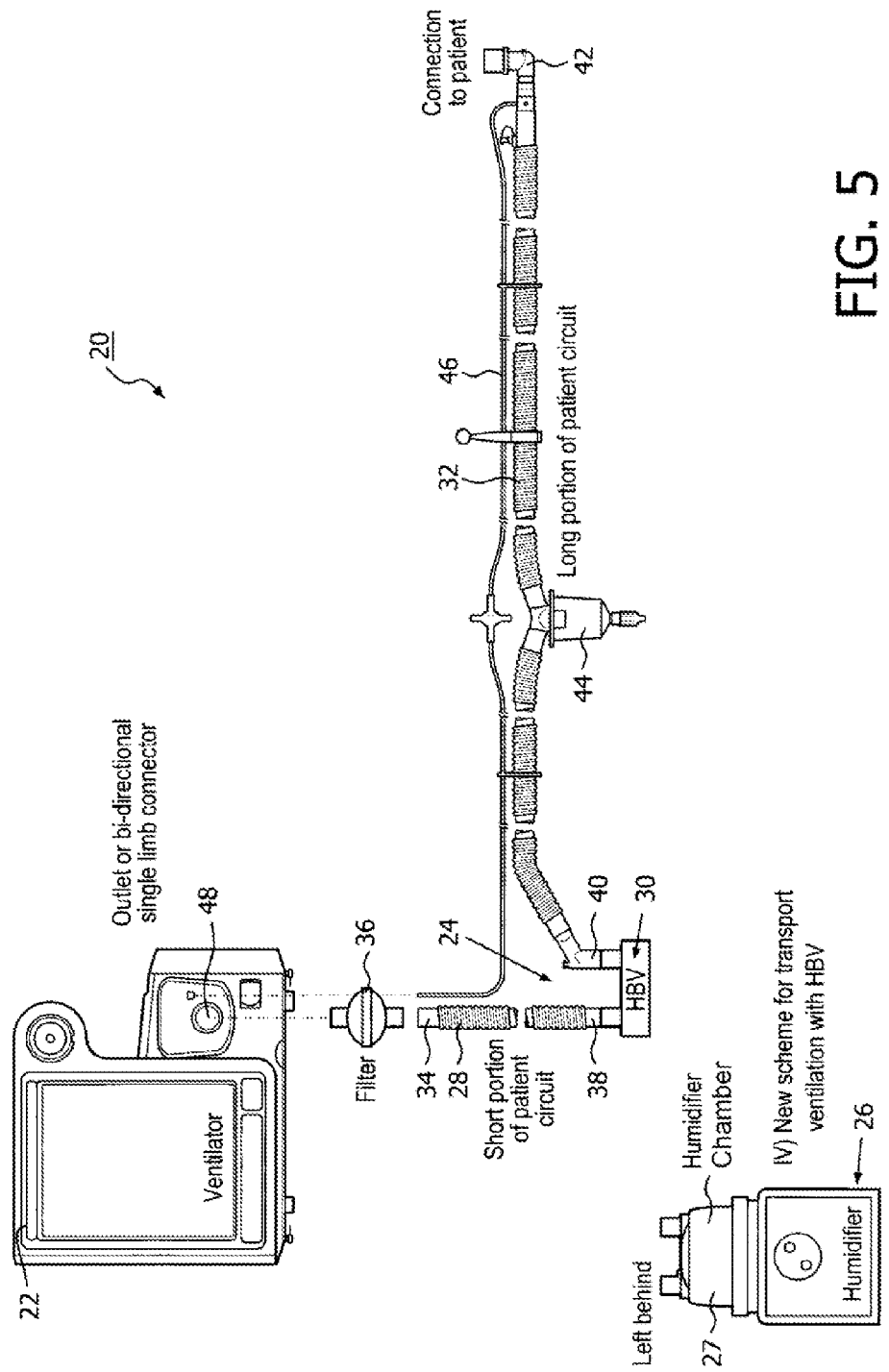
FIG. 5 illustrates a connection between the ventilator and the respiration circuit with the humidifier chamber disconnected from the respiration circuit using the bypass valve in accordance with an embodiment.

In the illustrated embodiment, the humidifier chamber 27 has an inlet port 78 and an outlet port 80. The first humidifier interface 62 of the bypass valve 30 is configured to interface and communicate with the inlet port 78 of the humidifier chamber 27 such that the fluid received from the inlet 60 of the bypass valve 30 may enter the humidifier chamber 27. The second humidifier interface 70 of the bypass valve 30 is configured to interface and communicate with the outlet port 80 of humidifier chamber 27 such that the second valve portion 52 receives the humidified fluid from the humidifier chamber 27 and directs the flow of fluid through the outlet 68. As shown in FIGS. 3 and 4, the inlet 60 of the first valve portion 50 is configured to connect to and communicate with the second end 38 of the first tube 28. The outlet 68 of the second valve portion 52 is configured to connect to and communicate with the first end 40 of the second tube 32. Accordingly, the fluid can flow from the ventilator 22 through the first tube 28 to the bypass valve 30 and flow from the bypass valve 30 through the second tube 32 to the patient interface for delivery to the subject. The bypass valve 30 can optionally direct the fluid through the humidifier chamber 27 to humidify the fluid when the bypass valve 30 is connected to the humidifier chamber 27. When the bypass valve 30 is not connected to the humidifier chamber 27, as shown in FIG. 5, such as during transport of the subject, the flow of fluid is directed through the conduit 54 of the bypass valve 30.

Referring back to FIG. 4, the first and second valve portions 50, 52, and the conduit 54 may be generally cylindrical, hollow structures that enable fluid to flow therethrough. The first valve portion 50 of the bypass valve 30 and the second valve portion 52 of the bypass valve 30 may be arranged such that they are substantially parallel to each other length-wise. The conduit 54 may be arranged such that the conduit is extending between the first and second valve portions 50, 52 in a substantially perpendicular direction thereto. Thus, the first and second valve portions 50, 52 and the conduit 54 may define a generally H-shaped configuration of the bypass valve 30. However, this example is not intended to be limiting, and it is contemplated that the configuration or arrangement of the bypass valve 30 may vary in other embodiments.

In some embodiments, the conduit 54 is adjustable in length to accommodate the size of the humidifier chamber 27 (e.g., the distance between the inlet port 78 and the outlet port 80). In such embodiments, the conduits 54 may be made of a flexible material that enables the conduits 54 to flex when required to lengthen the conduit 54 and to return to its original, default length when the conduit 54 no longer needs to be lengthened. Alternatively or additionally, the conduit 54 may be provided with a telescoping arrangement to enable the conduit 54 to increase in length when required. Accordingly, the bypass valve 30 may be used with a variety of humidifier chambers 27 with varying sizes. However, these examples of the conduit 54 are not intended to be limiting, and the conduit 54 may be made of any material that enables its length to be flexible or fixed.

In the embodiment shown in FIGS. 3 and 4, instead of directly connecting the first tube 28 to the inlet port 78 of the humidifier chamber 27 and the second tube 32 to the outlet port 80 of the humidifier chamber 27, the first tube 28 is connected to the inlet 60 of the bypass valve 30 and the second tube 32 is connected to the outlet 68 of the bypass valve 30. In such embodiment, the first humidifier interface 62 of the bypass valve 30 is connected to the inlet port 78 of the humidifier chamber 27 and the second humidifier interface 70 is connected to the outlet port 80 of the humidifier chamber 27. Accordingly, the inlet 60 and the outlet 68 of the bypass valve 30 may be similarly configured as the inlet port 78 and the outlet port 80 of the humidifier chamber 27. Furthermore, the first humidifier interface 62 of the bypass valve 30 may be similarly configured as the second end 38 of the first tube 28 and the second humidifier interface 70 may be similarly configured as the first end 40 of the second tube 32. In one embodiment, the inlet 60 of the bypass valve 30 and the outlet 68 of the bypass valve 30 are formed as conical male engaging members. These male engaging members may be of the type typically provided on the inlet and outlet of humidifier chambers, such as those complying with the ISO (International Organization of Standards) 5356-1 standard or other standards. For example, the inlet 60 and the outlet 68 each may have a diameter of about 22 mm, although the diameter may vary in other embodiments. In such embodiment, the first humidifier interface 62 and the second humidifier interface 70 are formed as conical female engaging members. These female engaging members may be of the type typically provided on the ends of the tubes of respiration circuits, such as those complying with the ISO (International Organization of Standards) 5356-1 standard or other standards. For example, the inlet 60 and the outlet 68 each may have a diameter of about 22 mm, although the diameter may vary in other embodiments. Accordingly, the female engaging members of the second end 38 of the first tube 28 and the first end 40 of the second tube 32 may be engaged with the male engaging members of the inlet 60 and outlet 68 of the bypass valve 30, respectively, to connect the first tube 28 and the second tube 32 to the bypass valve 30. Furthermore, the female engaging members of the first humidifier interface 62 and the second humidifier interface 70 may be engaged with the male engaging members of the inlet port 78 and outlet port 80 of the humidifier chamber 27 to connect the bypass valve 30 to the humidifier chamber 27.

In one embodiment, the first and second valve members 74, 76 may be biased in the first position such that the first and second valve members 74, 76 cover the first humidifier interface 62 and the second humidifier interface 70, respectively, until the bypass valve 30 is connected to the humidifier chamber 27. In one embodiment, the first and second valve members 74, 76 may be spring loaded or may have any other mechanical interaction with the engaging members of the inlet port 78 and outlet port 80 of the humidifier chamber 27 such that the first and second valve members 74, 76 moves to the second position when the first and/or second humidifier interfaces 62, 70 are connected to the inlet and outlet ports 78, 80 of the humidifier chamber 27. For example, in embodiments where the valve members 74, 76 are spring loaded, the connection of the first and second humidifier interfaces 62, 70 to the inlet and outlet ports 78, 80 of the humidifier chamber 27 may push against the bias of the spring to bring the first and second valve members 74, 76 to the second position. In one embodiment, the first and second valve members 74, 76 may include resilient material that biases the first and second valve members 74, 76 downwardly by resilience. The connection between the first and second humidifier interfaces 62, 70 to the inlet and outlet ports 78, 80 of the humidifier chamber 27 may push against the bias to bring the first and second valve members 74, 76 to the second position. In some embodiments, active mechanisms, such as pneumatics or electronics, may be used to move the first and second valve members 74, 76 between the second and first position. It is contemplated that a variety of manual, electrical, or mechanical means may be used to move the valves 74, 76 to the second position.

In some embodiments, when the humidifier 26 and its humidifier chamber 27 are disconnected from the respiration circuit 24, as shown in FIG. 5, a temporary or alternative source of humidification may be provided. For example, in one embodiment, a sponge or other device capable of imparting moisture to fluid passing through conduit 54 may be placed in the conduit 54 of the bypass valve 30. As mentioned above, in the embodiment shown in FIGS. 4 and 5, when the humidifier chamber 27 is disconnected from the respiration circuit 24, the fluid flows through the bypass valve 30 from the inlet 60 to the outlet 68 through the conduit 54. Accordingly, in such embodiment, the fluid that flows from the ventilator 22 to the subject may be humidified when the fluid passes through the conduit 54 of the bypass valve 30.

In one embodiment, the bypass valve 30 may be disposable or cleanable and reusable. In one embodiment, the bypass valve 30 is made of plastic. However, it is contemplated that the bypass valve 30 may be made of other materials, such as polymers, elastomers, or a combination thereof.

In one embodiment, the humidifier chamber 27 may be disposed on a cart or any other supporting structure, and the bypass valve 30 may be connected to the respiration circuit 24 and the ventilator 22 during transport of the subject. In such embodiment, the system 20 may be arranged such that when the humidifier chamber 27 is to be connected to the respiration circuit 24, the ventilator 22 may be placed on the cart or other supporting structure with the humidifier chamber 27 such that the first and second humidifier interfaces 62, 70 bypass valve 30 snaps into or connects to the inlet and outlet ports 78, 80, respectively, of the humidifier chamber 27. In such embodiment, the first tube 28 may not be necessary. For example, the bypass valve 30 may be directly connected to the ventilator 22 at the inlet 60 of the bypass valve 30 and the second tube 32 may be connected to the bypass valve 30 at the outlet 68 of the bypass valve 30 to deliver fluid to the patient. Thus, the humidifier chamber 27 and the ventilator 22 may share a common base or supporting structure to facilitate the connection/disconnection between the humidifier chamber 27 and the ventilator 22 and the respiration circuit 24.

Operation of the bypass valve 30 will be described in accordance with the embodiment shown in FIGS. 3-5. As shown in FIG. 3, the humidifier chamber 27 may be connected to the respiration circuit 24. In such embodiment, the ventilator 22 may provide a flow of fluid to the filter 36, which filters contaminants from the fluid. The fluid then flows through the first tube 28 to the bypass valve 30 via the connection between the second end 38 of the first tube 28 and the inlet 60 of the bypass valve 30. In this embodiment, the first and second humidifier interfaces 62, 70 of the bypass valve 30 are connected to the humidifier chamber 27. Thus, the first and second valve members 74, 76 are moved from their biased, first position to the second position wherein the first and second valve members 74, 76 cover the first and second conduit openings 64, 72, respectively. Thus, the flow path is formed from the inlet 60 to the outlet 68 of the bypass valve 30 through the humidifier chamber 27. Accordingly, the fluid flows into the bypass valve 30 at the inlet 60 of the bypass valve 30 and into the humidifier chamber 27 via the connection between the first humidifier interface 62 of the bypass valve 30 and the inlet port 78 of the humidifier chamber 27. The fluid is then humidified as it passes through the humidifier chamber 27. The humidified fluid then flows back into the bypass valve 30 via the connection between the outlet port 80 of the humidifier chamber 27 and the second humidifier interface 70 of the bypass valve 30. The fluid is then directed out of the bypass valve 30 and into the second tube 32 via the connection between the outlet 68 of the bypass valve 30 and the first end 40 of the second tube 32. The fluid then flows through the second tube 32 to the patient interface for delivery to the patient.

As shown in FIG. 5, the humidifier 26 and the humidifier chamber 27 may be disconnected from the respiration circuit 24, such as when the subject is to be transported or the humidifier chamber 27 is to be refilled or replaced. To disconnect the humidifier chamber 27 from the respiration circuit 24, the inlet and outlet ports 78, 80 may be disconnected from the first and second humidifier interfaces 62, 70, respectively. Accordingly, the first and second valve members 74, 76 are moved from their second position to the biased, first position wherein the first and second valve members 74, 76 cover the first and second humidifier interfaces 62, 70, respectively. Thus, the flow path is formed from the inlet 60 to the outlet 68 of the bypass valve 30 through the conduit 54. For example, after the fluid flows from the ventilator 22 into the bypass valve 30 through the inlet 60 of the bypass valve 30, the fluid flows through the first conduit opening 64 of the first valve portion 50 into the conduit 54 and then flows from the conduit 54 into the second valve portion 52 via the second conduit opening 72. The fluid is then directed out of the second valve portion 52 and into the second tube 32 via the connection between the outlet 68 of the bypass valve 30 and the first end 40 of the second tube 32. The fluid then flows through the second tube 32 to the patient interface for delivery to the patient.

It is contemplated that the bypass valve 30 may be used in systems 20 other than the embodiment shown in FIGS. 3-5. That is, the embodiment shown in FIG. 3 is a bidirectional single limb circuit, but the bypass valve 30 may be used in systems 20 having other configurations or arrangements (e.g. dual-limb).

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A valve configured to control a flow of fluid through the valve, the valve comprising:
   a conduit;
   a first valve portion disposed at a first end of the conduit, the first valve portion having an inlet configured to interface with a respiration circuit, a first humidifier interface configured to be removably connected to a humidifier chamber, and a first conduit opening in fluid communication with an interior of the conduit, the first valve portion being configured to define a switchable flow path between the inlet and either the first humidifier interface or the first conduit opening; and
   a second valve portion disposed at a second end of the conduit, the second valve portion having an outlet configured to interface with a respiration circuit, a second humidifier interface configured to be removably connected to the humidifier chamber, and a second conduit opening in fluid communication with the interior of the conduit, the second valve portion being configured to define a switchable flow path between the outlet and either the second humidifier interface or the second conduit opening,
   wherein the first valve portion and the second valve portion are configured such that:
      responsive to the first humidifier interface and the second humidifier interface to the humidifier chamber, the first valve portion and the second valve portion operatively form a flow path from the inlet to the outlet through the humidifier chamber, instead of through the conduit, and
      responsive to disconnecting the first humidifier interface and the second humidifier interface from the humidifier chamber, the first valve portion and the second valve portion operatively form a flow path from the inlet to the outlet through the conduit, instead of through the humidifier chamber.

2. The valve of claim 1, wherein the first valve portion comprises a first valve member operable to switch the switchable flow path between the inlet and either the first humidifier opening or the first conduit opening, and wherein the second valve portion comprises a second valve member operable to switch the switchable flow path between the outlet and either the second humidifier interface opening or the second conduit opening.

3. The valve of claim 2, wherein the first valve member is biased to cover the first humidifier interface and the second valve member is biased to cover the second humidifier interface opening such that the flow path is formed from the inlet to the outlet through the conduit.

4. The valve of claim 2, wherein when the flow path is formed from the inlet to the outlet through the humidifier chamber, the first valve member covers the first conduit opening and the second valve member covers the second conduit opening.

5. The valve of claim 1, wherein the conduit is adjustable in length such that the first humidifier interface opening and the second humidifier interface are connectable to the humidifier chamber.

6. A method for controlling a flow of fluid through a valve, the method comprising:
   receiving a flow of fluid from a respiration circuit at a first valve portion disposed at a first end of a conduit, the first valve portion having an inlet configured to interface with the respiration circuit, a first humidifier interface configured to be removably connected to a humidifier chamber, and a first conduit opening in fluid communication with the interior of the conduit, the first valve portion being configured to define a switchable flow path between the inlet and either the first humidifier interface or the first conduit opening; and receiving the flow of fluid from the humidifier chamber at a second valve portion disposed at a second end of the conduit, the second valve portion having a second humidifier interface configured to be removably connected to the humidifier chamber, a second conduit opening in fluid communication with the interior of the conduit, and an outlet configured to interface with a respiration circuit, the second valve portion being configured to define a switchable flow path between the outlet and either the second humidifier interface or the second conduit opening, wherein responsive to connecting the first humidifier interface and the second humidifier interface to the humidifier chamber, the first valve portion and the second valve portion operatively form a flow path for directing the flow of fluid between the inlet to the outlet through the humidifier chamber, instead of through the conduit, and responsive to disconnecting the first humidifier interface and the second humidifier interface from the humidifier chamber, the first valve portion and the second valve portion operatively form a flow path for directing the flow of fluid from the inlet of the first valve portion to the outlet of the second valve portion through the conduit, instead of through the humidifier chamber.

7. The method of claim 6, wherein the first valve portion comprises a first valve member operable to switch the switchable flow path between the inlet and either the first humidifier interface or the first conduit opening, and wherein the second valve portion comprises a second valve member operable to switch the switchable flow path between the outlet and either the second humidifier interface or the second conduit opening.

8. The method of claim 7, wherein the first valve member is biased to cover the first humidifier interface and the second valve member is biased to cover the second humidifier interface such that the flow path is formed from the inlet to the outlet through the conduit.

9. The method of claim 7, wherein further responsive to disconnecting the first humidifier interface and the second humidifier interface from the humidifier chamber, the first valve member covers the first humidifier interface and the second valve member covers the second humidifier interface.

10. The method of claim 6, wherein the conduit is adjustable in length such that the first humidifier interface and the second humidifier interface are connectable to the humidifier chamber.

11. A valve configured to control a flow of fluid through the valve, the valve comprising:
a first valve portion comprises:
means for receiving the flow of fluid from a respiration circuit;
first means for interfacing with a humidifier chamber to communicate the flow of fluid to the humidifier chamber;
a second valve portion comprising:
second means for interfacing with the humidifier chamber to receive the flow of fluid from the humidifier chamber;
means for directing the flow of fluid to the respiration circuit; and
means for connecting the first valve portion and the second valve portion, the first valve portion being disposed at a first end of the means for connecting for fluid communication therewith and the second valve portion being disposed at a second end of the means for connecting for fluid communication therewith, wherein the first valve portion defines a switchable flow path between the means for receiving and either the first means for interfacing or the means for connecting, and wherein the second valve portion defines a switchable flow path between the means for directing and either the second means for interfacing or the means for connecting, wherein the first valve portion and the second valve portion are configured such that:
means for switching in response to (i) connecting and (ii) disconnecting the first means for interfacing and the second means for interfacing with the humidifier chamber, respectively, a flow path between 1) a first flow path formed from the means for receiving to the means for directing through the humidifier chamber and not through the means for connecting, and 2) a second flow path formed from the means for receiving to the means for directing through the means for connecting, and not through the humidifier chamber, respectively.

12. The valve of claim 11, wherein the means for switching comprises 1) a first valve member operable to switch the switchable flow path between the means for receiving and either the first means for interfacing or the means for connecting, and 2) a second valve member operable to switch the switchable flow path between the means for directing and either the second means for interfacing or the means for connecting.

13. The valve of claim 12, wherein the first valve member is biased to cover the first means for interfacing and the second valve member is biased to cover the second means for interfacing.

14. The valve of claim 12, wherein the first valve portion further comprises a first conduit opening in fluid communication with an interior of the means for connecting and the second valve portion further comprises a second conduit opening in fluid communication with the interior of the means for connecting, and wherein when the flow path is in the first flow path, the first valve member covers the first conduit opening and the second valve member covers the second conduit opening.

15. The valve of claim 11, wherein the means for connecting is adjustable in length such that the first and second means for interfacing are connectable to the humidifier chamber.

* * * * *